(12) United States Patent
Swamy et al.

(10) Patent No.: US 10,420,516 B2
(45) Date of Patent: Sep. 24, 2019

(54) METHOD AND SYSTEM FOR DETERMINING RESPIRATION RATE

(71) Applicant: GENERAL ELECTRIC COMPANY, Schenectady, NY (US)

(72) Inventors: Gokul Swamy, Bangalore (IN); Sahika Genc, Niskayuna, NY (US); Ashish Anil Rao, Bangalore (IN); Abhijit Vishwas Patil, Bangalore (IN); Amod Jai Ganesh Anandkumar, Mysore (IN)

(73) Assignee: General Electric Company, Schenectady, NY (US)

( * ) Notice: Subject to any disclaimer, the term of this patent is extended or adjusted under 35 U.S.C. 154(b) by 636 days.

(21) Appl. No.: 15/035,632

(22) PCT Filed: Sep. 15, 2014

(86) PCT No.: PCT/US2014/055621
§ 371 (c)(1),
(2) Date: May 10, 2016

(87) PCT Pub. No.: WO2015/076916
PCT Pub. Date: May 28, 2015

(65) Prior Publication Data
US 2016/0262705 A1     Sep. 15, 2016

(30) Foreign Application Priority Data
Nov. 20, 2013    (IN) ........................... 5350/CHE/2013

(51) Int. Cl.
*A61B 5/0402*     (2006.01)
*A61B 5/08*     (2006.01)
(Continued)

(52) U.S. Cl.
CPC ............ *A61B 5/7278* (2013.01); *A61B 5/021* (2013.01); *A61B 5/0205* (2013.01);
(Continued)

(58) Field of Classification Search
CPC combination set(s) only.
See application file for complete search history.

(56) References Cited

U.S. PATENT DOCUMENTS 6,132,381 A     10/2000    Forbes et al.
2008/0027341 A1     1/2008    Sackner et al.
(Continued)

OTHER PUBLICATIONS

Nemati et. al. ("Data Fusion for Improved Respiration Rate Estimation," EURASIP Journal on Advances in Signal Processing, vol. 2010, Feb. 2010).*

(Continued)

*Primary Examiner* — Scott Luan (57) ABSTRACT

A method for determining a respiration rate of a subject, includes receiving a first signal and a second signal, each signal being representative of a physiological parameter of the subject. The method includes removing a cardiac artifact signal from the first signal and the second signal to generate a first processed signal and a second processed signal respectively. The method includes removing a motion artifact signal from the first processed signal and the second processed signal to generate a first periodic signal and the second processed signal respectively. The method further includes removing a residual noise signal from the first periodic signal and the second periodic signal to generate a first noise free signal and the second noise free signal respectively. The method includes generating a combined value from a first value and a second value based on the first noise free signal and the second noise free signal respectively.

17 Claims, 7 Drawing Sheets

(51) Int. Cl.
   *A61B 5/053* (2006.01)
   *A61B 5/00* (2006.01)
   *A61B 5/0205* (2006.01)
   *A61B 5/021* (2006.01)

(52) U.S. Cl.
   CPC .......... *A61B 5/0402* (2013.01); *A61B 5/0535* (2013.01); *A61B 5/0816* (2013.01); *A61B 5/725* (2013.01); *A61B 5/7207* (2013.01); *A61B 5/7225* (2013.01)

(56) References Cited

U.S. PATENT DOCUMENTS

| | | |
|---|---|---|
| 2008/0139955 A1 | 6/2008 | Hansmann et al. |
| 2009/0262006 A1 | 10/2009 | McNeill et al. |
| 2010/0130873 A1 | 5/2010 | Yuen et al. |
| 2011/0066041 A1 | 3/2011 | Pandia et al. |

OTHER PUBLICATIONS

Niizeki et. al. ("Unconstrained cardiorespiratory and body movement monitoring system for home care," Medical & Biological Engineering & Computing Jun. 2005, vol. 43).*
N. Vinh et. al. ("Comparison of two methods for demodulation of pulse signals—application in case of central sleep apnea," Journal of Science and Technology, vol. 49, No. 1, 2011).*
K. T. Sweeney et. al. ("Employing ensemble empirical mode decomposition for artifact removal: Extracting accurate respiration rates from ECG data during ambulatory activity," Jul. 2013 35th Annual International Conference of the IEEE Engineering in Medicine and Biology Society (EMBC), Osaka, 2013, pp. 977-980).*
International Search Report and Written Opinion for PCT/US2014/055621, dated Dec. 8, 2014, 8 pages.

* cited by examiner

METHOD AND SYSTEM FOR DETERMINING RESPIRATION RATE

CROSS-REFERENCE TO RELATED APPLICATIONS

This application is a filing under 35 U.S.C. 371 of international application number PCT/US2014/055621, filed Sep. 15, 2014, which claims priority to IN application number 5350/CHE/2013, filed Nov. 20, 2013, the entire disclosures of each which are hereby incorporated by reference.

BACKGROUND

The subject matter disclosed herein generally relates to determination of vital parameters from patient data. More specifically, the subject matter relates to a method and system for determination of respiration rate from a plurality of signals obtained from a patient.

Respiratory rate or the breathing rate is a potent indicator of patient health with relevance to respiratory and cardiovascular functions. In fact, respiratory rate exceeding 27 breaths per minute has been found to be a predictor of cardiac arrests in hospitals. Respiration rate measurement is useful in designing early warning scoring systems (EWS) for critical illness. In spite of its importance, respiration rate is often a neglected vital sign and is not routinely measured in clinical practice. One reason for this is that the manual measurement of respiration rate (e.g., counting breaths at the patient bedside) is a cumbersome process and also does not yield continuous estimates. That is, there are often periods of time where the patient is left unmonitored. As such, the manual measurement is associated with a high likelihood of missing important respiration events during the unmonitored period. Conventional methods used for unobtrusive continuous estimation of respiration rate suffer from poor measurement accuracy owing largely to algorithmic insufficiency. Presence of artifact signals such as cardiac artifacts and motion artifacts require computationally intensive and sophisticated signal processing techniques for deriving an estimate of respiration rate. Measurement inaccuracy can trigger false alarms often perpetrating the problem of "alarm fatigue", wherein caregivers have the tendency to ignore critical events with the belief that the measurement estimate is in all likelihood inaccurate.

There is a need for an enhanced system and method for estimation of respiration rate.

BRIEF DESCRIPTION

In accordance with one aspect of the present technique, a method for determining a respiration rate of a subject is disclosed. The method includes receiving a plurality of signals including a first signal and a second signal, each signal being representative of a physiological parameter of the subject. The method further includes processing the first signal to remove a cardiac artifact signal from the first signal and generate a first processed signal and processing the second signal to remove the cardiac artifact signal from the second signal and generate a second processed signal. The method further includes processing the first processed signal, using a polynomial fitting technique, to remove a motion artifact signal from the first processed signal and generate a first periodic signal and processing the second processed signal, using the polynomial fitting technique, to remove the motion artifact signal from the second processed signal and generate a second periodic signal. The method also includes processing the first periodic signal, using a spectral decomposition technique, to remove a residual noise signal from the first periodic signal and generate a first noise free signal and processing the second periodic signal, using the spectral decomposition technique, to remove the residual noise signal from the second periodic signal and generate a second noise free signal. The method further includes processing the first noise free signal, using a subspace-based technique, to generate a first value and processing the second noise free signal, using the subspace-based technique, to generate a second value and then determining a combined value based on the first value and the second value.

In accordance with one aspect of the present technique, a system for determining a respiration rate is disclosed. The system includes a signal acquisition system configured to receive a plurality of signals including a first signal and a second signal, each signal being representative of a physiological parameter of a subject. The system also includes at least one processor coupled to the signal acquisition system, the at least one processor is encoded with instructions to perform signal processing of the first and second signals. The instructions encoded in the at least one processor of the system include a cardiac-artifact removal module to process each signal among the first signal and the second signal to remove a cardiac artifact signal and generate a first processed signal and a second processed signal respectively. The instructions further include a motion-artifact removal module to process each signal among the first processed signal and the second processed signal, using a polynomial fitting technique, to remove a motion artifact signal and generate a first periodic signal and a second periodic signal respectively. The instructions also include a noise removal module to process each signal among the first periodic signal and the second periodic signal, using a spectral decomposition technique, to remove a residual noise signal and generate a first noise free signal and a second noise free signal respectively. The instructions further include an estimation module to process each signal among the first noise free signal and the second noise free signal, using a subspace-based technique, and generate a first value and a second value respectively. The instructions also include a combining module to determine a combined value based on the first value and the second value, the combined value being representative of the respiration rate of the subject.

In accordance with another aspect of the present technique, a non-transitory computer readable medium encoded with a program for determining a respiration rate of a subject, to instruct at least one processor is disclosed. The program instructs the at least one processor to receive a plurality of signals including a first signal and a second signal, each signal being representative of a physiological parameter of a subject. The program instructs the at least one processor to process the first signal to remove a cardiac artifact signal from the first signal and generate a first processed signal and process the second signal to remove the cardiac artifact signal from the second signal and generate a second processed signal. The program also instructs the at least one processor to process the first processed signal, using a polynomial fitting technique, to remove a motion artifact signal from the first processed signal and generate a first periodic signal and process the second processed signal, using the polynomial fitting technique, to remove the motion artifact signal from the second processed signal and generate a second periodic signal. The program also instructs the at least one processor to process the first periodic signal, using a spectral decomposition technique, to remove a residual noise signal from the first periodic signal and generate a first noise free signal and process the second periodic signal, using the spectral decomposition technique, to remove the residual noise signal from the second periodic signal and generate a second noise free signal. The program also instructs the at least one processor to process the first noise free signal, using a subspace-based technique, to generate a first value and process the second noise free signal, using the subspace-based technique, to generate a second value. The program further instructs the at least one processor to determine a combined value based on the first value and the second value, the combined value being representative of the respiration rate of the subject.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of the present invention disclose a system and a method for determining a respiration rate from a plurality of signals obtained by monitoring a patient. The technique involves receiving a plurality of signals including a first signal (for example, an impedance plethysmograph signal), a second signal (for example, an electrocardiograph signal), and a third signal (for example, an arterial blood pressure signal). Each signal is representative of physiological parameters of a subject The first signal, the second signal and the third signal are processed to remove a cardiac artifact signal to generate a first processed signal, a second processed signal, and a third processed signal respectively. The first processed signal, the second processed signal, and the third processed signals are processed using a polynomial fitting technique to remove a motion artifact signal to generate a first periodic signal, a second periodic signal, and a third periodic signal respectively. The first periodic signal, the second periodic signal, and the third periodic signal are processed using a spectral decomposition technique to remove a residual noise signal to generate a first noise free signal, a second noise free signal, and a third noise free signal respectively. The first noise free signal, the second noise free signal, and the third noise free signal are processed using a subspace-based technique to generate a first value, a second value, and a third value respectively. The technique further includes determining a combined value based on the first value, the second value and the third value. The combined value is representative of a respiration rate of the subject.

Figure 1:
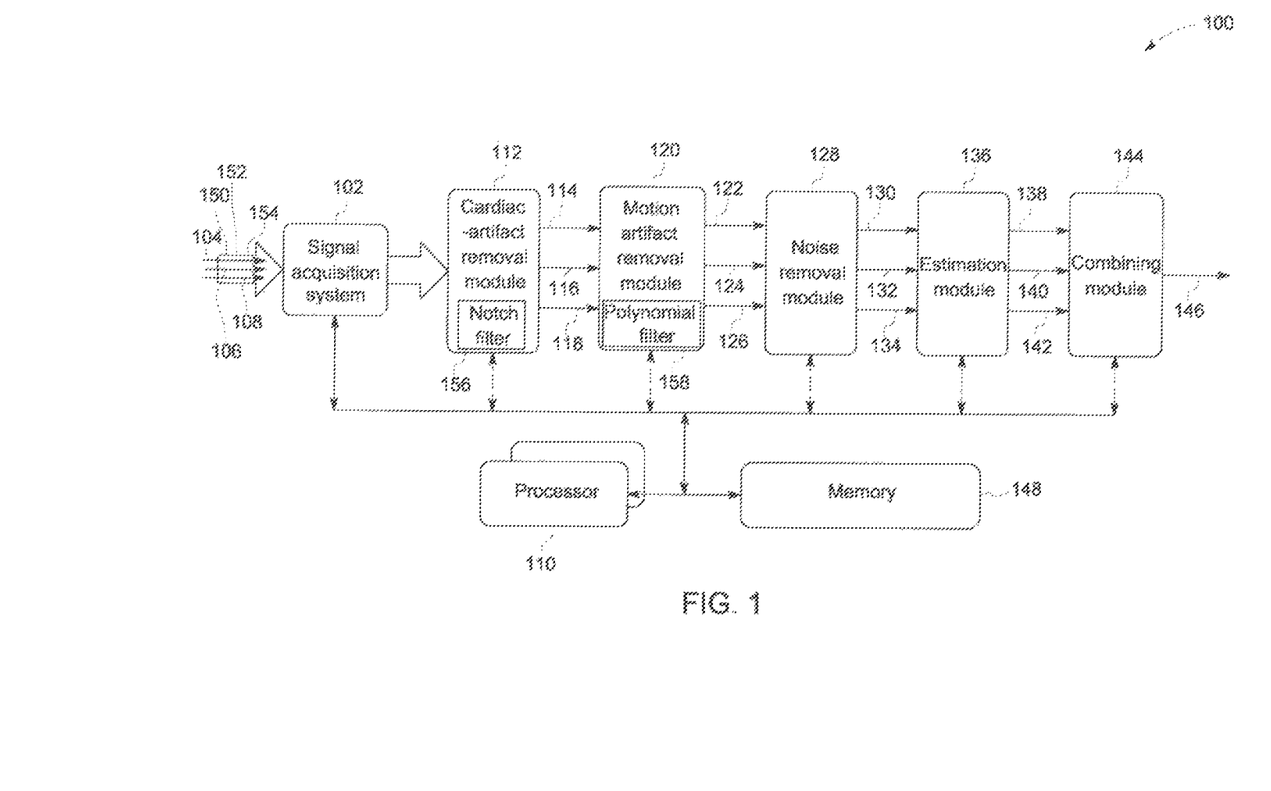
FIG. 1 is a block diagram of a system for determining a respiration rate of a subject in accordance with an exemplary embodiment.

FIG. 1 is a diagrammatic illustration of a system 100 for determining respiration rate of a subject in accordance with an exemplary embodiment. The system 100 includes a signal acquisition system 102, at least one processor 110, a cardiac-artifact removal module 112, a motion-artifact removal module 120, a noise removal module 128, an estimation module 136, and a combining module 144.

In the illustrated embodiment, the signal acquisition system 102 receives a plurality of signals, for example, a first signal 104, a second signal 106, and a third signal 108 which are vital signals indicative of physiological parameters of a subject. Specifically, the first signal 104, the second signal 106, and the third signal 108 are representative of physiological parameters of the subject. In other embodiments, the number and type of signals may vary depending on the application. The signal acquisition system 102 includes an analog-to-digital (A/D) convertor and signal conditioning circuitry (not shown) for generating a plurality of digital samples of each received signal 104, 106, 108. In an exemplary embodiment, the first signal 104 is an impedance plethysmograph (IP) signal, the second signal 106 is an electro cardio graph (ECG) signal, and the third signal 108 is an arterial blood pressure (ABP) signal. Each signal 104, 106, 108 may include a plurality of noise signals such as a cardiac artifact signal 150, a motion artifact signal 152, and a residual noise signal 154. The processor 110 is coupled to the signal acquisition system 102. In one embodiment, the processor 110 is encoded with instructions to perform processing of the first and second signals 104, 106 to compute a value indicative of the respiration rate of the subject. In another exemplary embodiment, the processor 110 is configured to perform processing of the first, second, and third signals 104, 106, 108 to compute a value indicative of the respiration rate of the subject. Specifically, the signal processing involves removing the cardiac artifact signal 150, the motion artifact signal 152, and the residual noise signal 154, from each signal 104, 106, 108. The processor 110 performs the processing of each signal 104, 106, 108 via the cardiac-artifact removal module 112, the motion-artifact removal module 120, the noise removal module 128, the estimation module 136, and the combining module 144.

The processor 110 may include at least one arithmetic logic unit, microprocessor, general purpose controller or other processor arrays to perform the desired computations. In one embodiment, the processor 110 represents a custom hardware configured to perform functions of one of the modules 112, 120, 128, 136, 144. In another embodiment, the processor 110 is a digital signal processor or a microcontroller. In an alternate embodiment, the processor 110 may also perform the functionality of the signal acquisition system 102. In some other embodiments, other type of processors, operating systems, and physical configurations are envisioned.

The system 100 also includes a memory 148 for storing instructions performed by the processor 110 and to store digital samples of each received signal 104, 106, 108. The memory 148 may be a non-transitory storage medium. For example, the memory 148 may be a dynamic random access memory (DRAM) device, a static random access memory (SRAM) device, flash memory or other memory devices. In one embodiment, the memory 148 may include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In one embodiment, the memory 148 may be communicatively coupled to the processor 110. In an alternate embodiment, the memory 148 is an on-board memory of the processor 110.

In one embodiment, the cardiac-artifact removal module 112 receives the first signal 104 and the second signal 106 from the signal acquisition system 102. The cardiac-artifact removal module 112 removes the cardiac artifact signal 150 to generate a first processed signal 114 and a second processed signal 116 respectively. In the illustrated embodiment, the cardiac-artifact-removal module 112 includes a notch filter 156. The notch filter 156 is used to remove a frequency component corresponding to a cardiac frequency from the first signal 104 and the second signal 106. In other embodiments, instead of the notch filter 156, other suitable filters may be employed to remove the cardiac artifact signal 150. In another embodiment, the cardiac-artifact removal module 112 additionally removes the cardiac artifact signal 150 from the third signal 108 to generate a third processed signal 118. In one embodiment, the cardiac-artifact removal module 112 is stored in the memory 148 and executed by the processor 110. In another embodiment, the cardiac removal module 112 is a customized hardware such as an ASIC or a FPGA.

In one embodiment, the motion-artifact removal module 120 receives the first processed signal 114 and the second processed signal 116 from the cardiac-artifact removal module 112. The motion-artifact removal module 120 removes the motion artifact signal 152 from the first processed signal 114 and the second processed signal 116 to generate a first periodic signal 122 and a second periodic signal 124 respectively. In the illustrated embodiment, the motion-artifact-removal module 120 includes a polynomial filter 158. The polynomial filtering is explained in greater detail with reference to a subsequent figure. In other embodiments, instead of the polynomial filter 158, other suitable filters may be employed to remove the motion artifact signal 152. In another embodiment, the motion-artifact removal module 120 additionally removes the motion artifact signal 152 from the third processed signal 118 to generate a third periodic signal 126. In one embodiment, the motion-artifact removal module 120 is stored in the memory 148 and executed by the processor 110. In another embodiment, the motion-artifact removal module 120 is a customized hardware such as an ASIC or a FPGA.

In one embodiment, the noise removal module 128 receives the first periodic signal 122 and the second periodic signal 124 from the motion-artifact removal module 120. The noise removal module 128 removes the residual noise signal 154 from the first periodic signal 122 and the second periodic signal 124 to generate a first noise free signal 130 and a second noise free signal 132 respectively. In the illustrated embodiment, the noise removal module 128 employs a spectral decomposition technique to remove the residual noise signal 154. The spectral decomposition technique is explained in greater detail with reference to a subsequent figure. In other embodiments, other suitable techniques may be employed to remove the residual noise signal 154. In another embodiment, the noise removal module 128 additionally removes the residual noise signal 154 from the third periodic signal 126 to generate a third noise free signal 134. In one embodiment, the noise removal module 128 is stored in the memory 148 and executed by the processor 110. In another embodiment, the noise removal module 128 is a customized hardware such as an ASIC or a FPGA.

In one embodiment, the estimation module 136 receives the first noise free signal 130 and the second noise free signal 132 from the noise removal module 128. The estimation module 136 processes the first noise free signal 130 and the second noise free signal 132 to determine a first value 138 and a second value 140 respectively. In one exemplary embodiment, the estimation module 136 employs a subspace-based technique to determine the first value 138 and the second value 140. The subspace-based technique involves estimating a wavelength duration based on the first noise free signal 130 and the second noise free signal 132. The subspace-based technique is explained in greater detail with reference to a subsequent figure. In another embodiment, the estimation module 136 additionally processes the third noise free signal 134 to generate a third value 142. In one embodiment, the estimation module 136 is stored in the memory 148 and executed by the processor 110. In another embodiment, the estimation module 136 is a customized hardware such as an ASIC or a FPGA.

In one embodiment, the combining module 144 receives the first value 138 and the second value 140 and generates a combined value 146. The combined value 146 is a weighted average value of the first value 138 and the second value 140. In another embodiment, the combining module 144 additionally receives the third value 142 and generates the combined value 146. In such an embodiment, the combined value 146 is a weighted average value of the first value 138, the second value 140, and the third value 142. In one embodiment, the combining module 144 is stored in the memory 148 and executed by the processor 110. In another embodiment, the combining module 144 is a customized hardware such as an ASIC or a FPGA.

Figure 2:
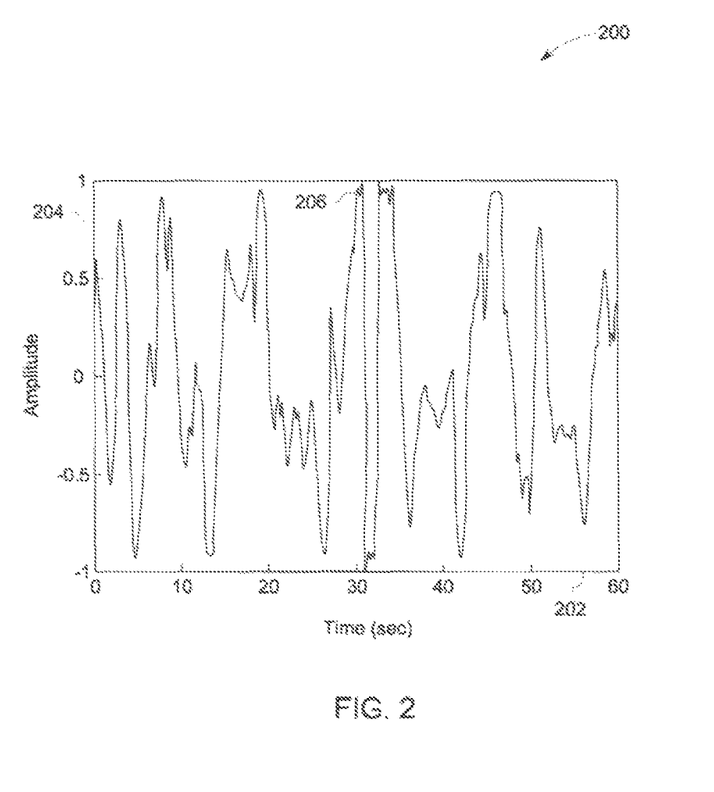
FIG. 2 is a graph illustrating an impedance plethysmograph waveform used for determining a respiration rate in accordance with an exemplary embodiment.

FIG. 2 is a graph 200 illustrating the first signal indicative of a plethysmograph waveform 206 used to determine a respiration rate in accordance with an exemplary embodiment. The x-axis 202 is representative of time in seconds and y-axis 204 is representative of the amplitude of the plethysmograph waveform 206. The waveform 206 includes a combination of the cardiac artifact signal 150, the motion artifact signal 152, and the residual noise signal 154. In one exemplary embodiment, the notch filter 156 is used for removing the cardiac artifact signal from the waveform 206. The notch filter may be a band stop filter having a high fractional bandwidth (also referred to as a "Q value" which is a ratio of a center frequency to the bandwidth of the filter). In one embodiment, the notch filter is a single pole filter. In one specific embodiment, a two-zero, two-pole transfer function may be used to design the notch filter. In another embodiment, the notch filter may be an adaptive filter. The first notch filter is used to filter the first signal to generate the first processed signal 114.

Similarly, notch filter 156 may be used to remove the cardiac artifact signal 150 from the second signal and the third signal to generate the second processed signal 116 and the third processed signal 118 respectively. In another embodiment, separate notch filters may be used to remove the cardiac artifact signal from the first, second, and third signals. In such embodiments, the notch filters may have the same transfer function and different poles and zeroes.

Figure 3:
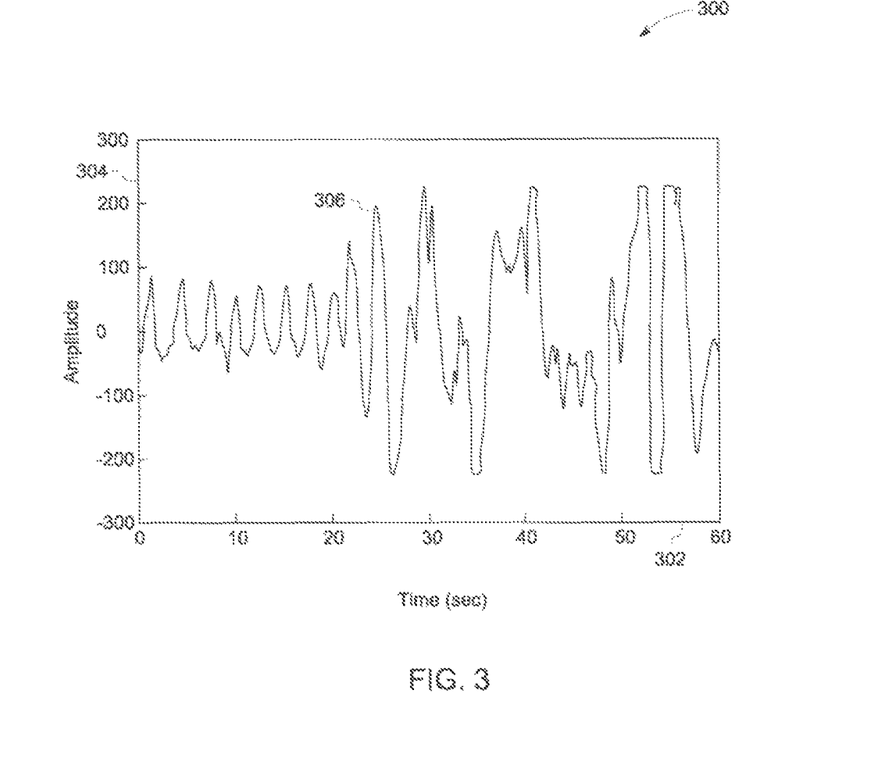
FIG. 3 is a graph illustrating a first processed signal indicative of a waveform in accordance with an exemplary embodiment.

FIG. 3 is a graph 300 illustrating the first processed signal 114 indicative of a waveform 306 used to determine a respiration rate in accordance with an exemplary embodiment. The x-axis 302 is representative of time in seconds and the y-axis 304 is representative of amplitude. The waveform 306 is processed using a polynomial fitting technique to remove the motion artifact signal 152. In one embodiment, the polynomial fitting technique involves using a linear least squares method, for example, to generate a first Savitzky Golay filter, for example. The first Savitzky Golay filter is then used to process the first processed signal to generate the first periodic signal. In other embodiments, other polynomial fitting techniques may be employed.

A Savitzky Golay filter of order N and having a half window width M is obtained from a first row of a matrix H represented by:

$$H = (AA^T)^{-1} A \quad (1)$$

where A is a vandermonde matrix of the order (2M+1)×(N+1) constructed based on a plurality of values from a vector [−M, −M+1, . . . , −1, 0, 1, . . . , M−1, M]. The matrix A is represented by:

$$A = \begin{bmatrix} -M^0 & -M^1 & \ldots & -M^N \\ (-M+1)^0 & (-M+1)^1 & \ldots & (-M+1)^N \\ \vdots & \vdots & \ldots & \vdots \\ M^0 & M^1 & \ldots & M^N \end{bmatrix} \quad (2)$$

where 2M>N. The superscript T is representative of transposition operation for the matrix A. The first periodic signal 122 is obtained by filtering the first processed signal 114, using the Savitzky Golay filter.

Similarly, the polynomial fitting technique may be used to remove the motion artifact signal 152 from the second processed signal 116 and the third processed signal 118 to generate the second periodic signal 124 and the third periodic signal 126 respectively. In certain embodiments, separate Savitzky Golay filters may be used to remove the motion artifact signal from the first, second, and third processed signal. In such embodiments, different values of M may be used to determine Savitzky Golay filters for processing the first, second, and the third processed signals. The Savitzky Golay filters of same order N have the same structure, but the coefficients of the filters may differ as the matrix A corresponding to different Savitzky Golay filters differs depending on the choice of M.

Figure 4:
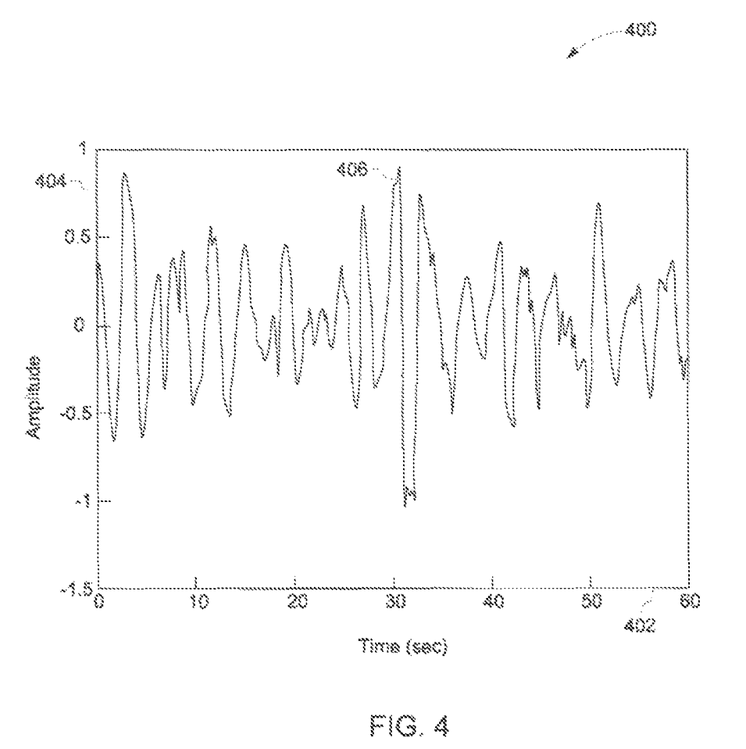
FIG. 4 is a graph illustrating a first periodic signal indicative of a waveform in accordance with an exemplary embodiment.

FIG. 4 is a graph 400 illustrating the first periodic signal 122 indicative of a plethysmograph waveform 406 used to determine a respiration rate in accordance with an exemplary embodiment. The x-axis 402 is representative of time in seconds and the y-axis 404 is representative of amplitude. The waveform 406 is processed using a spectral decomposition technique, for example, to remove the residual noise signal and generate the first noise free signal. In one embodiment, the spectral decomposition technique involves identifying a spectral component of the residual noise signal of the waveform 406. In another embodiment, the spectral decomposition technique involves identifying noise free version of the waveform 406.

In one embodiment, the spectral component may be determined using a singular spectrum analysis (SSA) technique. The singular spectrum analysis technique involves retaining a portion of a singular spectrum determined via a singular value decomposition (SVD) technique. The SVD technique involves determining one or more principle components of the waveform 406.

The singular value decomposition (SVD) technique of a time series matrix A is represented by:

$$[U,S,V] = \text{SVD}(A) \quad (3)$$

where, U and V are the matrices comprising the left and right eigenvectors and S is a diagonal matrix having the corresponding singular values providing a singular spectrum of the matrix A. The time series matrix A, constructed from samples y(n) of the waveform 406, is represented by:

$$A = \begin{bmatrix} y(L) & \ldots & y(1) & y(0) \\ y(L+1) & \ldots & y(2) & y(1) \\ \vdots & \vdots & \vdots & \vdots \\ y(2L-1) & \ldots & y(L) & y(L-1) \\ y(2L) & \ldots & y(L+1) & y(L) \end{bmatrix} \quad (4)$$

where L+1 is the order of the matrix A and y(k) is the kth sample of the signal y(n). The singular value decomposition technique involves retaining "r" principle components of the L+1 principle components. The reconstructed embedded time series matrix A* is determined by:

$$A^* = US^*V \quad (5)$$

where $$S^* = \begin{bmatrix} S\{1,1\} & 0 & & & & \\ 0 & S\{2,2\} & & & & \\ & & \ddots & & & \\ & & & S\{r,r\} & & \\ & & & & 0 & \\ & & & & & \ddots \\ & & & & & & 0 \end{bmatrix} \quad (6)$$

where S(k,k) is the kth singular value of the matrix A.

A reconstructed signal derived from entries of A* matrix, is representative of the first noise free signal. In another embodiment, the spectral component may be determined using an empirical mode decomposition (EMD) technique. The EMD technique involves representing the waveform 406 as a sum of a plurality of intrinsic mode functions and a residual signal component. One or more of the plurality of intrinsic mode functions, referred herein as principal modes, are used to generate the reconstructed signal. Similarly, the second periodic signal and the third periodic signal are processed using the spectral decomposition technique to generate the second noise free signal and the third noise free signal respectively.

Figure 5:
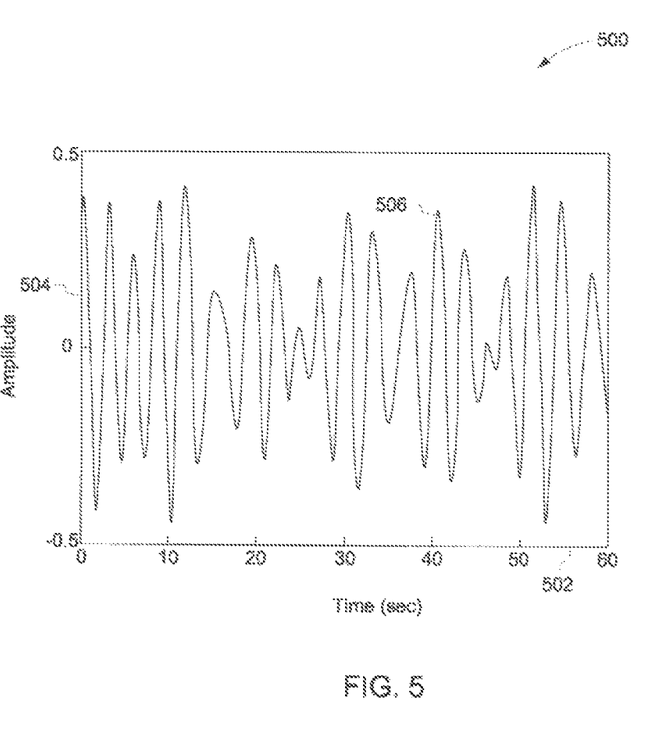
FIG. 5 is a graph illustrating a first noise free signal indicative of a waveform in accordance with an exemplary embodiment.

FIG. 5 is a graph 500 illustrating the first noise free signal 130 indicative of a waveform 506 used to determine a respiration rate in accordance with an exemplary embodiment. The x-axis 502 is representative of time in seconds and the y-axis 504 is representative of amplitude. The waveform 506 has a low frequency periodic signal and a plurality of high frequency components. The low frequency periodic signal is representative of a first value indicative of the respiration rate of the subject. The first value indicative of the respiration rate is determined using a subspace-based technique, for example. In one embodiment, the subspace-based technique is a MUSIC technique. In another embodiment, the subspace-based technique is an ESPRIT technique.

The spectral estimation by MUSIC technique is represented by:

$$G(w) = \frac{1}{\sum_{i=p+1}^{N} |e^H v_i|^2} \quad (7)$$

where $v_i$ are the noise eigenvectors of an autocorrelation matrix corresponding to the waveform 506. The autocorrelation matrix has an order N, a signal subspace of dimension p, and a noise subspace of dimension N−p. The vector $e=[1, e^{jw}, e^{2jw}, \ldots, e^{j(N-1)w}]^T$, where, $e^{jw}$ is the complex exponential function, w is an angular frequency and H is indicative of hermitian operator. From equation (7), a frequency w at which G(w) is prominent is determined. A period of a signal component having the frequency w is representative of the first respiration rate.

The spectral estimation by ESPRIT technique is represented by:

$$T\psi T^{-1} = \varphi \quad (8)$$

where, ψ is an operator that maps a subspace of the signal space into another subspace, T is a matrix of eigen vectors, and φ is diagonal matrix of eigen values of the matrix ψ. The eigen values of the matrix ψ may be used to determine the frequency components. A frequency component corresponding to a dominant eigen value of the matrix ψ is representative of the first respiration rate.

Similarly, the second noise free signal 132 and the third noise free signal 134 have a low frequency periodic signal representative of the second value and the third value indicative of the respiration rate of the subject.

Figure 6:
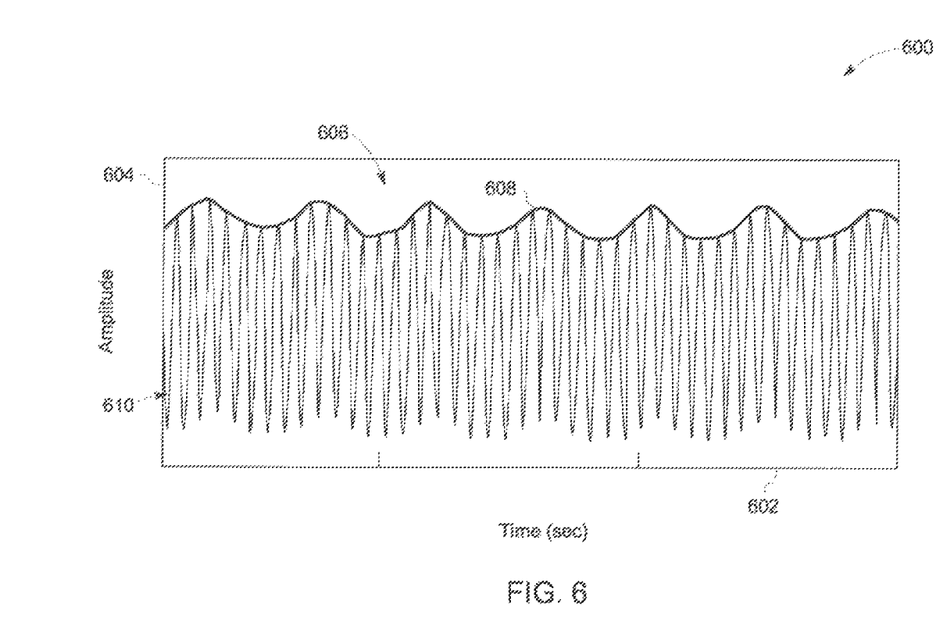
FIG. 6 is a graph illustrating a third noise free signal indicative of a waveform in accordance with an exemplary embodiment.

FIG. 6 is a graph 600 illustrating the third noise free signal 134 representative of a waveform 606 used to determine a respiration rate in accordance with an exemplary embodiment. The x-axis 602 is representative of time in seconds and the y-axis 604 is representative of amplitude. The waveform 606 has a low frequency periodic signal 608 and a plurality of high frequency components 610. The low frequency periodic signal 608 is representative of the third value indicative of the respiration rate of the subject.

Figure 7:
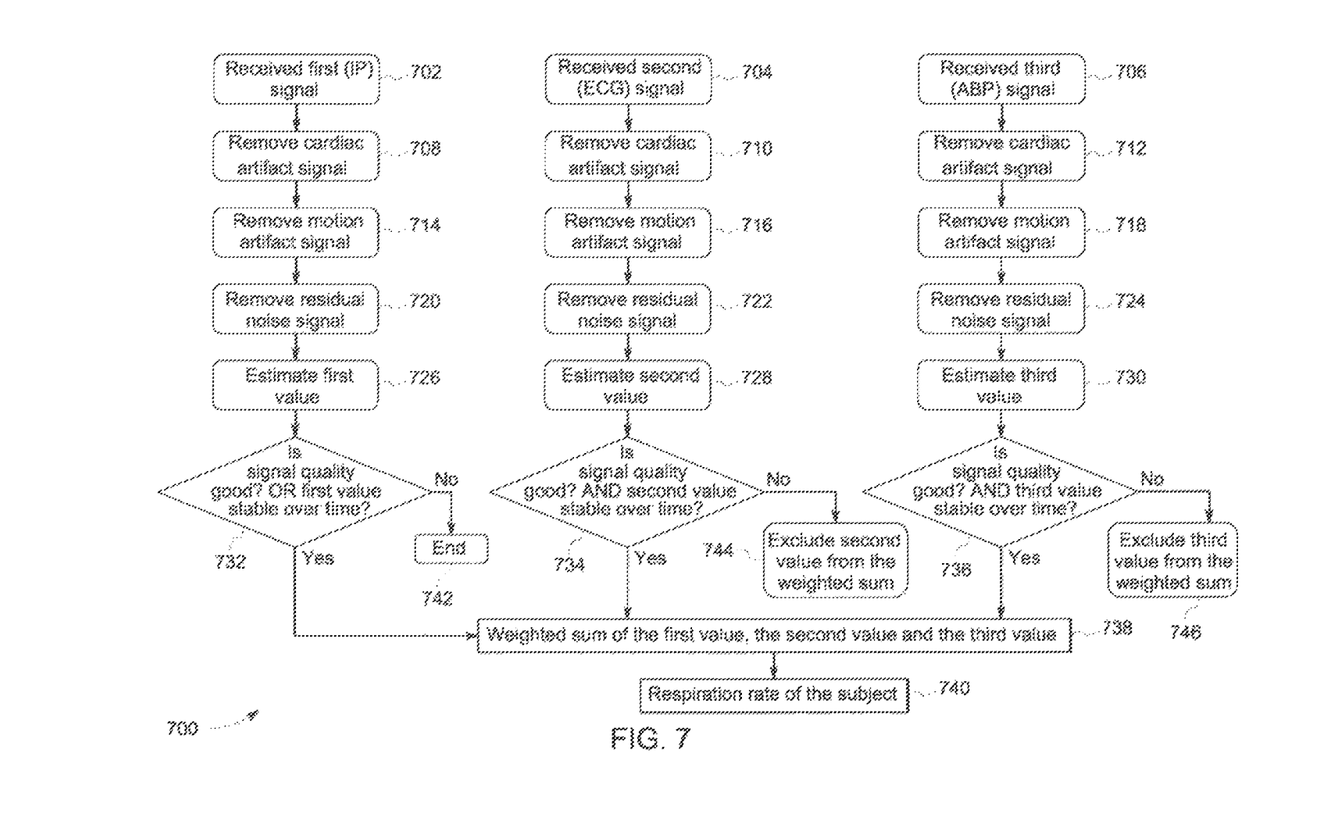
FIG. 7 is a flow chart illustrating a method for determining a respiration rate of a subject in accordance with an exemplary embodiment.

FIG. 7 is a flow chart 700 illustrating a plurality of steps involved in determining a respiration rate of a subject in accordance with an exemplary embodiment. The method involves receiving a plurality of signals from a subject and then processing each received signal to determine the respiration rate of the subject. Specifically, the plurality of signals includes a first signal 702, a second signal 704, and a third signal 706. In one embodiment, the first signal is an impedance plethysmograph signal, the second signal is an ECG signal, and the third signal is an arterial blood pressure (ABP) signal.

The first signal is processed by removing a cardiac artifact signal 708 from the first signal, via a notch filter, to generate a first processed signal. The first processed signal is processed by removing a motion artifact signal from the first processed signal 714 via a polynomial filter such as a Savitzky Golay filter, for example, to generate a first periodic signal. The first periodic signal is processed by removing a residual noise signal 720 from the first periodic signal, using a spectral decomposition method such as singular value decomposition (SVD) technique, for example, to generate a first noise free signal. In an alternative embodiment, an Empirical Mode Decomposition (EMD) technique may be used for performing spectral decomposition of the first periodic signal. A first value representative of the respiration rate of the subject, is estimated 726 from the first noise free signal.

The second signal is processed by removing a cardiac artifact signal 710 from the second signal, via a notch filter, to generate a second processed signal. The second processed signal is processed by removing a motion artifact signal 716 from the second processed signal via a polynomial filter such as a Savitzky Golay filter, to generate a second periodic signal. The second periodic signal is processed by removing a residual noise signal 722 from the second periodic signal, using spectral decomposition technique such as singular value decomposition (SVD) technique, to generate a second noise free signal. In an alternative embodiment, an Empirical Mode Decomposition (EMD) technique may be used for performing spectral decomposition of the second periodic signal. A second value representative of the respiration rate of the subject, is estimated 728 from the second noise free signal.

The third signal is processed by removing a cardiac artifact signal 712 from the third signal via a notch filter to generate a third processed signal. The third processed signal is processed by removing a motion artifact signal 718 from the third processed signal via a polynomial filter such as a Savitzky Golay filter to generate a third periodic signal. The third periodic signal is processed by removing a residual noise signal 724 from the third periodic signal, using spectral decomposition technique such as a singular value decomposition (SVD) technique, to generate a third noise free signal. In an alternative embodiment, an Empirical Mode Decomposition (EMD) technique may be used for performing spectral decomposition of the third periodic signal. A third value representative of the respiration rate of the subject, is estimated 730 from the third noise free signal.

The first value, the second value, and the third value are combined to determine an estimate of the respiration rate of the subject. In an exemplary embodiment, the first value is used to determine an estimate of the respiration rate of the subject. In such an embodiment, the second value and the third value may be used optionally. In an alternate embodiment, the first value is considered based on a quality of the first signal. In such an embodiment, the second value and the third value are considered based on the quality of the second and third signals respectively. In one specific embodiment, the first value, the second value, and the third value are considered if a variation of the first value, the second value, and the third value with respect to time, is within a predefined threshold value.

In the illustrated embodiment, a quality of the first signal and a rate of change of the first value are evaluated 732. If the quality of the first signal is satisfactory, the first value is used. Alternatively, if the rate of change of the first value is less than a threshold, the first value is used. If the evaluation 732 is not satisfactory, the processing is concluded 742 without determining the respiration rate. Further, a quality of the second signal and a rate of change of the second value are evaluated 734. If the quality of the second signal is satisfactory and if the rate of change of the second value is less than a threshold, the second value is used. If the evaluation 734 is not satisfactory, the second value is excluded from the weighted sum 744. Similarly, a quality of the third signal and a rate of change of the third value are evaluated 736. If the quality of the third signal is satisfactory and if the rate of change of the third value is less than a threshold, the third value is used. If the evaluation 736 is not satisfactory, the third value is excluded from the weighted sum 746. A weighted average value of the plurality of values among the first value, the second value, and the third value, is computed 738 to determine the respiration rate of the subject 740.

In an exemplary embodiment, a weighted average value is determined for each signal from the first signal, the second signal, and the third signal. A first weighted value is determined based on a first signal-to-noise ratio of the first signal. A second weighted value is determined based on a second signal-to-noise ratio of the second signal. The weighted average value is determined based on the first weighted value, the first value, the second weighted value, and the second value. In another exemplary embodiment, a third weighted value is determined based on a third signal-to-noise ratio of the third signal. The weighted average value is determined based on the first weighted value, the first value, the second weighted value, the second value, the third weighted value, and the third value. It should be noted herein that the first weighted value, the second weighted value, and the third weighted value may also be determined based on any other signal quality indicators of the first signal, the second signal and the third signal respectively.

The weighted average value is represented by:

$$rr = \delta_1 \frac{\Sigma_i \delta_i rr_i SQI_i}{\Sigma_i SQI_i} \qquad (9)$$

where rr is an estimate of the respiration rate of the subject, $rr_i$ is a rate of change of the respiration rate from the ith signal, $SQI_i$ is a signal quality indicator of ith signal, and $\delta_i$ is the delta function corresponding to the ith signal. The $\delta_i$ for the ith signal is defined as:

$\delta_i$=1 if $rr_i < T_i$ && $SQI_i > E_i$ when $i$=2,3

1 if $rr_i < T_i \| SQI_i > E_i$ when $i$=1

0 otherwise  (10)

where $T_i$ is an upper limit of the rate of change of the respiration rate for the ith signal and $E_i$ is a lower limit of the signal quality indicator for the ith signal. When the first value is not considered for determining the respiration rate, the value $\delta_1$ is zero and the respiration rate is not determined (Equation (8) generates a zero value) irrespective of the signal quality of the second and the third signal. When the first value is considered for determining the respiration rate, the value $\delta_1$ is equal to one. The second value and the third value are considered for determining the respiration rate based on the values of $\delta_2$ and $\delta_3$ respectively.

Exemplary embodiments disclosed herein disclose a technique for determining a respiration rate from a plurality of vital signals of a subject. The plurality of vital signals includes an impedance plethysmograph signal, the ECG signal and the arterial blood pressure signal. The cardiac artifact signal, the motion artifact signal, and the residual noise signal are removed from each of the plurality of signals, using exemplary signal processing techniques. A first value, a second value, and a third value representative of respiration rate derived from the plurality of signals are generated. The plurality of values are combined to enhance a quality of estimate of the respiration rate of the subject.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the invention are not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the inventions may include only some of the described embodiments. Accordingly, the inventions are not to be seen as limited by the foregoing description, but are only limited by the scope of the appended claims.

What is claimed as new and desired to be protected by Letters Patent of the United States is:

1. A method, comprising:
   receiving a plurality of signals comprising a first signal and a second signal, each signal being representative of physiological parameters of a subject;
   (i) processing the first signal to remove a cardiac artifact signal from the first signal and generate a first processed signal and processing the second signal to remove the cardiac artifact signal from the second signal and generate a second processed signal;
   (ii) processing the first processed signal using a polynomial fitting technique to remove a motion artifact signal from the first processed signal and generate a first periodic signal and processing the second processed signal using the polynomial fitting technique to remove the motion artifact signal from the second processed signal and generate a second periodic signal;
   (iii) processing the first periodic signal using a spectral decomposition technique to remove a residual noise signal from the first periodic signal and generate a first noise free signal and processing the second periodic signal using the spectral decomposition technique to remove the residual noise signal from the second periodic signal and generate a second noise free signal;
   (iv) processing the first noise free signal using a subspace-based MUSIC technique or ESPRIT technique to generate a first value and processing the second noise free signal using the subspace-based technique to generate a second value; and
   determining a combined value based on the first value and the second value, wherein the combined value is representative of a respiration rate of the subject.

2. The method of claim 1, wherein the plurality of signals further comprises a third signal, wherein the first signal is an impedance plethysmograph signal, the second signal is an electro cardiograph signal, and the third signal is an arterial blood pressure signal.

3. The method of claim 2, further comprising:
   processing the third signal to remove the cardiac artifact signal from the third signal and generate a third processed signal;
   processing the third processed signal using the polynomial fitting technique to remove the motion artifact signal from the third processed signal and generate a third periodic signal;
   processing the third periodic signal using the spectral decomposition technique to remove the residual noise signal from the third periodic signal and generate a third noise free signal;

processing the third noise free signal using the subspace-based technique to generate a third value; and
determining the combined value based on the first value, the second value, and the third value.

4. The method of claim 1, wherein determining the combined value comprises:
determining a first weighted value for the first value based on a first signal-to-noise ratio of the first signal;
determining a second weighted value for the second value based on a second signal-to-noise ratio of the second signal; and
determining a weighted average value based on the first weighted value, the first value, the second weighted value, and the second value.

5. The method of claim 1, wherein the polynomial fitting technique comprises a linear least squares method.

6. The method of claim 1, wherein the spectral decomposition technique comprises determining a spectral component corresponding to at least one of the residual noise signal and the first noise free signal, in the first periodic signal.

7. The method of claim 6, wherein determining the spectral component comprises:
constructing a time series matrix based on a plurality of sample values of the first periodic signal; and
performing a singular value decomposition of the time series matrix.

8. The method of claim 6, wherein determining the spectral component comprises determining a principal mode of the first periodic signal, using an empirical mode decomposition (EMD) technique.

9. A system comprising:
a signal acquisition system configured to receive a plurality of signals comprising a first signal and a second signal, each signal being representative of physiological parameters of a subject; and
at least one processor coupled to the signal acquisition system, the at least one processor encoded with instructions to perform signal processing of the first and second signals, the instructions including:
a cardiac-artifact removal module to process each signal among the first signal and the second signal to remove a cardiac artifact signal and generate a first processed signal and a second processed signal respectively;
a motion-artifact removal module to process each signal among the first processed signal and the second processed signal, using a polynomial fitting technique, to remove a motion artifact signal and generate a first periodic signal and a second periodic signal respectively;
a noise removal module to process each signal among the first periodic signal and the second periodic signal, using a spectral decomposition technique, to remove a residual noise signal and generate a first noise free signal and a second noise free signal respectively;
an estimation module to process each signal among the first noise free signal and the second noise free signal, using a subspace-based MUSIC technique or ESPRIT technique, and generate a first value and a second value respectively; and
a combining module to determine a combined value based on the first value and the second value, wherein the combined value is representative of a respiration rate of the subject.

10. The system of 9, wherein the signal acquisition system is configured to receive a third signal, wherein the first signal is an impedance plethysmograph signal, the second signal is an electro cardiograph signal, and the third signal is an arterial blood pressure signal.

11. The system of claim 10, wherein the cardiac-artifact removal module, the motion-artifact removal module, the noise removal module, and the estimation module generates a third processed signal, a third periodic signal, a third noise free signal, and a third value respectively, and determines the combined value based on the first value, the second value, and the third value.

12. The system of claim 9, wherein the combining module determines the combined value by:
determining a first weighted value for the first value based on a first signal-to-noise ratio of the first signal;
determining a second weighted value for the second value based on a second signal-to-noise ratio of the second signal; and
determining a weighted average value based on the first weighted value, the first value, the second weighted value, and the second value.

13. The system of claim 9, wherein the cardiac-artifact removal module comprises a notch filter.

14. The system of claim 9, wherein the motion-artifact removal module comprises a Savitzky Golay filter.

15. The system of claim 9, wherein the noise removal module uses the spectral decomposition technique comprising an empirical mode decomposition (EMD) technique.

16. The system of claim 9, wherein the noise removal module uses the spectral decomposition technique comprising a singular spectrum analysis (SSA) technique.

17. A non-transitory computer readable medium encoded with a program to instruct at least one processor to:
receive a plurality of signals comprising a first signal and a second signal, each signal being representative of physiological parameters of a subject;
(i) process the first signal to remove a cardiac artifact signal from the first signal and generate a first processed signal and process the second signal to remove the cardiac artifact signal from the second signal and generate a second processed signal;
(ii) process the first processed signal using a polynomial fitting technique to remove a motion artifact signal from the first processed signal and generate a first periodic signal and process the second processed signal using the polynomial fitting technique to remove the motion artifact signal from the second processed signal and generate a second periodic signal;
(iii) process the first periodic signal using a spectral decomposition technique to remove a residual noise signal from the first periodic signal and generate a first noise free signal and process the second periodic signal using the spectral decomposition technique to remove the residual noise signal from the second periodic signal and generate a second noise free signal;
(iv) process the first noise free signal using a subspace-based MUSIC technique or ESPRIT technique to generate a first value and process the second noise free signal using the subspace-based technique to generate a second value; and
determine a combined value based on the first value and the second value, wherein the combined value is representative of a respiration rate of the subject.

* * * * *